United States Patent [19]

Nakanishi et al.

[11] Patent Number: 4,657,860

[45] Date of Patent: Apr. 14, 1987

[54] PROCESS FOR PRODUCING L-LYSINE BY FERMENTATION

[75] Inventors: Toshihide Nakanishi; Toshihiko Hirao; Minoru Sakurai, all of Hofu, Japan

[73] Assignee: Kwowa Hakko Kogyo Co., Ltd., Tokyo, Japan

[21] Appl. No.: 754,923

[22] Filed: Jul. 15, 1985

Related U.S. Application Data

[63] Continuation of Ser. No. 405,406, Aug. 5, 1982, abandoned.

[30] Foreign Application Priority Data

Aug. 10, 1981 [JP] Japan .................................. 56-125006

[51] Int. Cl.[4] ...................... C12P 13/08; C12N 15/00; C12R 1/13; C12R 1/15
[52] U.S. Cl. .................................. 435/115; 435/172.1; 435/840; 435/843
[58] Field of Search ..................... 435/115, 172.1, 840, 435/843

[56] References Cited

U.S. PATENT DOCUMENTS

| | | |
|---|---|---|
| 2,979,439 | 4/1961 | Kinoshita et al. .................... 435/115 |
| 3,687,810 | 8/1972 | Kurihara et al. ..................... 435/115 |
| 3,707,441 | 12/1972 | Shiio et al. ............................ 435/115 |
| 3,825,472 | 7/1974 | Kubotz et al. ........................ 435/115 |
| 3,905,867 | 9/1975 | Kurimura et al. ................... 435/115 |
| 4,066,501 | 1/1978 | Tosaka et al. ........................ 435/115 |
| 4,169,763 | 10/1979 | Nakayama et al. ................. 435/115 |
| 4,411,997 | 10/1983 | Shimazaki et al. .................. 435/115 |

Primary Examiner—David M. Naff
Attorney, Agent, or Firm—Antonelli, Terry & Wands

[57] ABSTRACT

Production of L-lysine is carried out by a process which involves culturing a mutant microorganism having increased L-lysine productivity belonging to the genus Corynebacterium or Brevibacterium and having a resistance to at least one of purine analog and pyrimidine analog.

8 Claims, No Drawings

PROCESS FOR PRODUCING L-LYSINE BY FERMENTATION

This is a continuation of application Ser. No. 405,406, filed Aug. 5, 1982, now abandoned.

This invention relates to a process for producing L-lysine by fermentation. More particularly, the present invention relates to a process for producing L-lysine by fermentation, which is characterized by culturing a microorganism belonging to the genus Corynebacterium or Brevibacterium and having both an ability to produce L-lysine and a resistance to at least one of purine analog and pyrimidine analog in a nutrient medium, and recovering L-lysine formed and accumulated from the culture liquor.

An object of the present invention is to provide a process for producing, by fermentation, L-lysine which is one of the essential amino acids and which has a great demand as a medicament, additive to animal feed or food, etc., at an industrially low cost.

Heretofore, the following processes have been known as the processes for producing L-lysine by fermentation: Processes using homoserine (or methionine and threonine)-requiring mutants (Japanese Published Examined Patent Application No. 6499/61 and U.S. Pat. No. 2,979,439) or other compounds-requiring mutants (Japanese Published Examined Patent Application Nos. 28677/73, 21078/76, 34477/76 (U.S. Pat. No. 3,825,472), 1040/80, Japanese Published Unexamined Patent Application Nos. 8692/81 and 9784/80) of microorganisms belonging to the genus Corynebacterium, Brevibacterium, Arthrobacter, Bacillus, etc., processes using mutants having a resistance to various chemicals (Japanese Published Examined Patent Application Nos. 28078/73 (U.S. Pat. No. 3,707,441), 1833/78, 43591/78, Japanese Published Unexamined Patent Application Nos. 86089/78, 9394/78, 9785/80 (U.S. Pat. No. 3,687,810); and processes using microorganisms having combined properties thereof.

As a result of various studies for obtaining strains having an increased L-lysine productivity, the present inventors have found that a strain capable of producing L-lysine belonging to the genus Corynebacterium or Brevibacterium endowed with a resistance to at least one of purine analog and pyrimidine analog has a remarkably improved ability to produce L-lysine, thus having completed the present invention. The fact that the productivity of L-lysine is rapidly increased by using a strain having a resistance to at least one of purine analog and pyrimidine analog in the production of L-lysine by fermentation has been found initially by the present inventors.

The present invention will be described in more detail below.

In the present process, any strain may e used so long as it belongs to the genus Corynebacterium or Brevibacterium and has both an ability to produce L-lysine and a resistance to at least one of purine analog and pyrimidine analog. That is, in the present invention, either a strain obtained by endowing a strain belonging to the genus Corynebacterium or Brevibacterium and having an ability to produce L-lysine with a resistance to at least one of purine analog and pyrimidine analog, or a strain obtained by endowing a strain belonging to the genus Corynebacterium or Brevibacterium and having a resistance to at least one of a purine analog and a pyrimidine analog with an ability to produce L-lysine may be used. As the strain belonging to the genus Corynebactrium or Brevibacterium and having an ability to produce L-lysine, for example, strains capable of producing L-lysine having one or a combination of a requirement for nutrients (for example, homoserine, methionine, threonine, histidine, proline, alanine, leucine, isoleucine, valine, serine, glutamic acid, pantothenic acid, nicotinic acid amide, acetic acid, adenine, hypoxanthine, inositol, and their combinations), a resistance to various amino acid analogs (for example, analogs of lysine, threonine, methionine, leucine, isoleucine, valine, aspartic acid, tryptophane, histidine, and their combinations), and a resistance to other chemicals (for example, various antibiotics, sulfa drugs, various organic acids, quinone compounds, quinoline compounds, and their combinations, etc.) may be mentioned. Accordingly, a strain to be used in the present invention may be obtained by endowing such a strain capable of producing L-lysine as mentioned above with a property of resistance to at least one of a purine analog and a pyrimidine analog, or a strain capable of producing L-lysine obtained by endowing a strain belonging to the genus Corynebacterium and having a property of resistance to at least one of a purine analog and a pyrimidine analog with various nutrients requirement, a resistance to various amino acid analogs or a resistance to other chemicals as mentioned above may also be used in the present invention. Further, the strain to be used in the present invention may have any other property of contributing to L-lysine productivity than the properties mentioned above.

As a resistance to a purine analog, a resistance to 6-mercaptoguanine, 8-azaguanine, 2-fluoroadenine, tubercidin, 6-methylpurine, 8-azaxanthine, 8-azaadenine, 8-mercaptoguanosine, 6-mercaptoguanosine, 2-aminopurine, 2-amino-6-mercaptopurine, decoyinin, psicofuranine, etc., is mentioned, and as a resistance to a pyrimidine analog, a resistance to 5-bromouracil, 6-azauracil, 5-fluorouracil, 5-bromo-2-deoxyuridine, 2-thiouracil, 6-methyl-2-thiouracil, amicetin, etc., is mentioned.

Mutants useful in carrying out the present invention are derived from parent strains belonging to the genus Corynebacterium or Brevibacterium known as an L-glutamic acid-producing strain, such as *Corynebacterium glutamicum* ATCC 13032, *Corynebacterium acetoacidophilum* ATCC 13870, *Brevibacterium lactofermentum* ATCC 13869, *Brevibacterium flavum* ATCC 14067, etc.

*Corynebacterium glutamicum* H-3107 (hereinafter referred to as H-3107) (FERM BP-144), *Corynebacterium glutamicum* H-3290 (hereinafter referred to as H-3290) (FERM BP-156) and *Brevibacterium lactofermentum* H-3114 (hereinafter referred to as H-3114) (FERM BP-146) may be mentioned as examples of the strain having a resistance to a purine analog.

*Corynebacterium glutamicum* H-3106 (hereinafter referred to as (FERM BP-143) *Corynebacterium glutamicum* H-3289 (hereinafter referred to as H-3289) FERM BP-157), *Brevibacterium lactofermentum* H-3113 (hereinafter referred to as H-3113) (FERM BP-145) and *Brevibacterium lactofermentum* H-3291 (FERM BP-155) may be mentioned as examples of a strain having a resistance to a pyrimidine analog.

Of these strains, the strains H-3107 and H-3106 are mutants obtained by suspending cells of *Corynebacterium glutamicum* FERM P-3634 (hereinafter referred to as P-3634) (NRRL-B-8183) (having a requirement for homoserine and leucine and having a resistance to thialysine and sulfamethazine) capable of producing lysine in a 0.1N tris-maleate buffer solution (pH 6.0) in a concentration of $10^8$ cells/ml, adding thereto N-methyl-N'-nitro-N-nitrosoguanidine to make a final concentration of 0.2 mg/ml, allowing the suspension to stand at room temperature for 30 minutes, then smearing the suspension on a flat agar plate of minimal medium of the following composition containing 0.4 mg/ml of 6-mercaptoguanosine (6-MG) or on a flat agar plate of minimal medium of the similar composition containing 0.4 mg/ml of 6-azauracil (6-AU), and then selecting mutants from growing colonies. The two strains (H-3107 and H-3106) are clearly discriminated from the parent strain (P-3634) in that the two possess a resistance to 6-mercaptoguanosine and to 6-azauracil, respectively, as shown in Table 1.

The strains H-3289 and H-3290 are selected as mutants having a resistance to 5-bromouracil and to 6-methylpurine, respectively, from P-3634, and the strains H-3114, H-3114, H-3113 and H-3291 are selected as mutants having a resistance to 6-mercaptoguanosine, 6-azauracil and to 5-bromouracil from *Brevibacterium lactofermentum* H-3056 (hereinafter referred to as H-3056) (FERM BP-154) (having a resistance to thialysine and a requirement for leucine and partial requirement for homoserine) in the same mutation treatment as described above. The strains H-3289 and H-3290 are clearly discriminated from the parent strain (P-3634) and also the strains H-3114, H-3113 and H-3291 are clearly discriminated from the parent strain (H-3056), as shown in Table 1.

phosphate, etc., urea, amines, other nitrogen-containing compounds and peptone, meat extract, yeast extract, corn steep liquor, casein hydrolyzate, soybean meal acid-hydrolyzate, various microbial cells, digest of microbial cells, etc., may be used.

As the inorganic materials, potassium dihydrogen phosphate, dipotassium hydrogen phosphate, magnesium phosphate, magnesium sulfate, sodium chloride, ferrous sulfate, manganese sulfate, calcium carbonate, etc., are used. When a microorganism to be used in the present invention requires specific nutrients for growth, an appropriate amount of the nutrients are added to the medium. In some cases, these nutrients are added as components of the natural substances exemplified as the nitrogen source.

Further, the productivity of L-lysine by the present microorganism can be in some cases enhanced by adding other various additives, for example, various antibiotics, α-aminobutyric acid, cysteine, leucine, leucine fermentation liquor, aspartic acid, glutamic acid, etc., to the medium.

Culturing is carried out under aerobic conditions, for example, by shaking culture, agitation submerged culture, etc. The temperature for culturing is generally 20°–40° C., and the pH of the medium is in a range of 3 to 9, and is preferably maintained at around neutral, but culturing can be carried out under conditions which are out of this range so long as the microorganism used can grow. The pH of the medium is adjusted with calcium carbonate, acid or alkali solution, pH buffering agent, etc. Usually, after culturing for 1 to 6 days, L-lysine is formed and accumulated in the resulting culture liquor.

TABLE 1

| (++: sufficient growth; +: growth to some extent; −: no growth) | | | | | | | | | |
|---|---|---|---|---|---|---|---|---|---|
|  | P-3634 | H-3107 | H-3106 | H-3289 | H-3290 | H-3056 | H-3114 | H-3113 | H-3291 |
| Nothing added | ++ | ++ | ++ | ++ | ++ | ++ | ++ | ++ | ++ |
| 6-Mercaptoguanosine |  |  |  |  |  |  |  |  |  |
| 100 μg/ml | − | ++ | − |  |  | − | ++ | − |  |
| 500 μg/ml | − | + | − |  |  | − | ++ | − |  |
| 6-Azauracil |  |  |  |  |  |  |  |  |  |
| 100 μg/ml | − | − | ++ |  |  | − | − | ++ |  |
| 500 μg/ml | − | − | + |  |  | − | − | + |  |
| 6-Methylpurine |  |  |  |  |  |  |  |  |  |
| 100 μg/ml | − |  |  | − | ++ | − |  |  | − |
| 400 μg/ml | − |  |  | − | + | − |  |  | − |
| 5-Bromouracil |  |  |  |  |  |  |  |  |  |
| 1000 μg/ml | − |  |  | ++ | − | − |  |  | ++ |
| 2000 μg/ml | − |  |  | + | − | − |  |  | + |

Composition of the flat agar plate of minimal medium is as follows.

10 g/l of glucose, 4 g/l of ammonium chloride, 1 g/l of KH$_2$PO$_4$, 3 g/l of K$_2$HPO$_4$, 0.4 g/l of MgSO$_4$.7H$_2$O, 0.01 g/l of FeSO$_4$.7H$_2$O, 0.01 g/l of MnSO$_4$.4H$_2$O, 2 g/l of urea, 50 μg/l of biotin and 20 g/l of agar. pH: 7.2.

Any of synthetic medium and natural medium may be used as the medium for the present invention, so long as it properly contains a carbon source, inorganic materials and other necessary nutrients which are assimilable by the strains utilized.

As the carbon source, various carbohydrates, such as glucose, fructose, sorbitol, glycerol, sucrose, starch, starch hydrolyzate, molasses, fruit juice, etc., organic acids such as acetic acid, fumaric acid, lactic acid, succinic acid, etc., and alcohols such as ethanol, methanol, etc., may be used.

As the nitrogen source, ammonia, inorganic and organic ammonium salts, such as ammonium chloride, ammonium sulfate, ammonium acetate, ammonium After the completion of culturing, precipitates, such as cells, are removed from the culture liquor and L-lysine can be recovered from the culture liquor by use of the conventional methods, such as ion exchange resin treatment, concentration, adsorption, salting-out in combination.

Practice of specific embodiments of the present invention is illustrated by the following representative examples.

EXAMPLE 1

H-3107 (having a resistance to 6-mercaptoguanosine) is used as a seed strain.

The seed strain is inoculated in a 300 ml-Erlenmeyer flask containing 20 ml of a seed medium (pH 7.2) comprising 40 g/l of glucose, 3 g/l of urea, 1.5 g/l of KH$_2$PO$_4$, 0.5 g/l of K$_2$HPO$_4$, 0.5 g/l of MgSO$_4$.7H$_2$O, 50 μg/l of biotin, 20 g/l of peptone and 5 g/l of yeast extract, and cultured at 30° C. for 24 hours. Then, 2 ml of the resulting seed culture is put into a 300 ml-Erlenmeyer flask containing 20 ml of a fermentation medium (pH 7.2) comprising 90 g/l of blackstrap molasses (as glucose), 20 g/l of soybean meal acid hydrolyzate (as soybean meal), 5 g/l of ammonium sulfate, 3 g/l of urea, 0.5 g/l of $MgSO_4.7H_2O$, 0.7 g/l of $K_2HPO_4$ and 30 g/l of $CaCO_3$, and cultured with shaking at 30° C. for 3 days. As a result, 38 g/l of L-lysine (as mnohydrochloride, which shall be hereinafter applied) is formed and accumulated in the culture liquor. Amount of L-lysine in culturing parent strain P-3634 under the same conditions as a control is 34 g/l.

After the completion of culturing, 1 l of the culture liquor of H-3107 is centrifuged. The resulting supernatant is adjusted to pH 1.5 with sulfuric acid, and passed through a column of Diaion SK-1B (H+ form, trade mark of strongly acidic ion-exchange resin made by Mitsubishi Chemical Industries, Ltd.) to adsorb thereon L-lysine. After washing the column with water, L-lysine is eluted with a dilute aqueous ammonia to collect and concentrate L-lysine-containing fractions. After pH of the concentrate is adjusted to 2 with hydrochloric acid, the concentrate is cooled, while adding ethanol thereto, whereby L-lysine is crystallized. Thus, 30.4 g of crystals of L-lysine is obtained.

EXAMPLE 2

Strains shown in Table 2 are, respectively, inoculated in the same seed media as in Example 1 and cultured at 30° C. for 24 hours. Then, 2 ml of each of the resulting seed culture liquor is put into a 300 ml-Erlenmeyer flask containing 20 ml of a fermentation medium (pH 7.2) Comprising 90 g/l of glucose, 20 g/l of soybean meal acid hydrolyzate (as soybean meal), 5 g. of ammonium sulfate, 3 g/l of urea, 0.5 g/l of $MgSO_4.7H_2O$, 1 gl of $KH_2PO_4$, 50 µg/l of biotin, 200 µg/ml of thiamine hydrochloride, 10 mg/l of $FeSO_4.7H_2O$, 10 mg/l of $MnSO_4.4H_2O$ and 20 g/l of $CaCO_3$, and cultured with stirring at 30° C. for 3 days. Amounts of L-lysine accumulated in the culture liquors are given in Table 2.

TABLE 2

| Strain | L-lysine |
| --- | --- |
| Corynebacterium glutamicum | |
| P-3634 | 33.0 g/l |
| H-3106 | 36.0 g/l |
| H-3289 | 35.0 g/l |
| H-3290 | 34.5 g/l |
| Brevibacterium lactofermentum | |
| H-3056 | 31.0 g/l |
| H-3114 | 35.0 g/l |
| H-3113 | 34.0 g/l |
| H-3291 | 34.0 g/l |

EXAMPLE 3

H-3106 is used as a seed strain.

The seed strain is inoculated in a 2 l-Erlenmeyer flask containing 300 ml of the same seed medium as in Example 1 and cultured with shaking at 30° C. for 24 hours. Then, 2 l of the resulting seed culture is put into a 30 l-jar fermenter containing 10 l of a fermentation medium comprising 100 g/l of blackstrap molasses (as glucose), 0.3 g/l of $MgSO_4.7H_2O$, 0.7 g/l of $KH_2PO_4$, 3 g/l of urea, 18 g/l of soybean meal acid hydrolyzate (as soybean meal) and 1.4% (v/v) of a leucine fermentation liquor prepared in advance as hereinafter described, and cultured at an aeration rate of 10 l/minute, a stirring speed of 400 r.p.m. and 30° C., for 48 hours, while adjusting pH of culture liquor at 6.8 with 22% aqueous ammonia. As a result, 43 g/l of L-lysine is formed and accumulated in the culture liquor. When a parent strain P-3634 is cultured in the same manner as above, 37 g/l of L-lysine is obtained.

The leucine fermentation liquor used in said fermentation medium is prepared in the following manner.

Corynebacterium glutamicum ATCC 21885, a leucine producing strain, is inoculated in a 5 l-jar fermenter containing 3 l of seed medium (pH 7.2) comprising 50 g/l of glucose, 10 g/l of peptone, 10 g/l of yeast extract, 5 g/l of corn steep liquor, 2.5 g/l of NaCl, 3 g/l of urea and 50 µg/l of biotin, and cultured with aeration stirring at an aeration rate of 3 l/minute, a stirring speed of 600 r.p.m., and 30° C. for 17 hours. Then, 1 l of the resulting speed culture is put into a 30 l-jar fermenter containing 10 l of a fermentation medium (pH 6.8) comprising 5 g/l of ammonium acetate, 2 g/l of $KH_2PO_4$, 0.5 g/l of $MgSO_4.7H_2O$, 0.1 g/l of $FeSO_4.7H_2O$, 0.01 g/l of $MnSO_4.4H_2O$, 50 µg/l of biotin and 100 ηg/l of thiamine hydrochloride, and cultured with aeration-stirring at an aeration rate of 10 l/minute, a stirring speed of 400 r.p.m., and 30° C. for 60 hours. In the course of culturing, pH of the culture liquor is adjusted to 6.8 by using a mixed solution containing 7% ammonium acetate and 38% acetic acid as a continuous feed. Thus, a leucine fermentation liquor containing 15.3 g/l of leucine is obtained, which is used as a portion of said fermentation medium for L-lysine.

What is claimed is:

1. A biologically pure culture of the microorganism Corynebacterium glutamicum H-3107 (FERM BP-144), which microorganism, when cultured, produces L-lysine.

2. A biologically pure culture of the microorganism Corynebacterium glutamicum H-3106 (FERM BP-143), which microorganism, when cultured, produces L-lysine.

3. A biologically pure culture of the microorganism Corynebacterium glutamicum H-3290 (FERM BP-156), which microorganism, when cultured, produces L-lysine.

4. A biologically pure culture of the microorganism Brevibacterium lactofermentum H-3114 (FERM BP-146), which microorganism, when cultured, produces L-lysine.

5. A biologically pure culture of the microorganism Brevibacterium lactofermentum H-3113 (FERM BP-145), which microorganism, when cultured, produces L-lysine.

6. A biologically pure culture of the microorganism Brevibacterium lactofermentum H-3291 (FERM BP-155), which microorganism, when cultured, produces L-lysine.

7. A biologically pure culture of the microorganism Corynebacterium glutamicum H-3289 (FERM BP-157), which microorganism, when cultured, produces L-lysine.

8. A process for producing L-lysine by fermentation, which comprises culturing Corynebacterium glutamicum H-3107 (FERM BP-144), Corynebacterium glutamicum H-3106 (FERM BP-143), Corynebacterium glutamicum H-3290 (FERM BP-156), Corynebacterium glutamicum H-3289 (FERM BP-157), Brevibacterium lactofermentum H-3114 (FERM BP-146), Brevibacterium lactofermentum H-3113 (FERM BP-145) or Brevibacterium lactofermentum H-3291 (FERM BP-155) in a nutrient medium, forming and accumulating L-lysine in the resulting culture liquor, and recovering the L-lysine therefrom.

* * * * *